United States Patent [19]

Zysman et al.

[11] Patent Number: 5,290,565

[45] Date of Patent: Mar. 1, 1994

[54] COMPOSITION FOR PROMOTING HEALING

[75] Inventors: Alexandre Zysman; Henri Sebag, both of Paris; Guy Vanlerberghe, Montjay-La-Tour; Rose-Marie Handjani; Alain Ribier, both of Paris, all of France

[73] Assignee: L'Oreal, Paris, France

[21] Appl. No.: 882,423

[22] Filed: May 13, 1992

Related U.S. Application Data

[60] Continuation of Ser. No. 684,697, Apr. 12, 1991, abandoned, which is a division of Ser. No. 497,696, Mar. 23, 1990, abandoned.

[30] Foreign Application Priority Data

Apr. 6, 1989 [FR] France .................. 89 04526

[51] Int. Cl.$^5$ .............................. A61K 9/127
[52] U.S. Cl. .................. 424/450; 424/DIG. 13; 428/402.2; 514/937; 514/941
[58] Field of Search ............... 514/675, 723, 937, 941; 424/450; 428/402.2

[56] References Cited

U.S. PATENT DOCUMENTS

4,217,344 8/1980 Vanlerberg et al. ............... 424/450
4,917,951 4/1990 Wallach ........................ 428/402.2

FOREIGN PATENT DOCUMENTS

0000340 1/1980 Japan.
2198947 6/1988 United Kingdom.

*Primary Examiner*—Thurman K. Page
*Assistant Examiner*—G. S. Kishore
*Attorney, Agent, or Firm*—Cushman, Darby & Cushman

[57] ABSTRACT

Composition for promoting healing containing, as a healing agent, nonionic vesicles obtained from a lipid mixture containing at least one nonionic lipid having the formula;

$$RO\!-\!(CH_2\!-\!CHOH\!-\!CH_2O)_{\overline{2}}\,H,$$

wherein R is either at least one $C_{16}$-$C_{18}$ radical, or R'CO wherein R' is at least one $C_{15}$-$C_{17}$ alkyl radical, in combination with cholesterol and, optionally, dicetylphosphate or tetracetylphospate.

This composition can be used topically to accelerate the scarring of wounds.

2 Claims, No Drawings

COMPOSITION FOR PROMOTING HEALING

This is a continuation of application Ser. No. 07/684,697, filed Apr. 12, 1991, now abandoned which is a division of application Ser. No. 07/497,696 filed Mar. 23, 1990, now abandoned.

This invention relates to a composition which promotes the healing of living animal tissue, and in particular the healing of the human dermis.

As is well known, it is very important to obtain a rapid healing of wounds reaching the dermis and to rapidly obtain scars possessing a high rupture strength in order to avoid any reopening of the wound. In this way, the mobility of patients after operations or accidents is more quickly ensured.

According to the present invention, it has been found that certain nonionic vesicles make it possible to accelerate healing significantly. The nonionic vesicles are, as is well-known, bounded by layers composed of non-ionic lipids, in an arrangement in which said layers surround a closed space.

The present invention relates to a composition for promoting healing, characterized by the fact that it contains, dispersed in an aqueous phase D, vesicles obtained from at least one nonionic lipid having the formula:

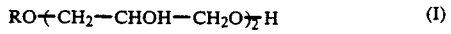

$$RO-(CH_2-CHOH-CH_2O)_{\overline{n}}H \quad (I)$$

wherein R represents either a $C_{16}-C_{18}$ alkyl radical or a mixture of several of these radicals, or an R'CO radical, wherein R' is a $C_{15}-C_{17}$ alkyl radical, or a mixture of several of these radicals, the said nonionic lipid being combined with cholesterol, and the total vesicular lipid concentration in the composition ranging from 5 to 25 percent by weight, and preferably from 6 to 10 percent by weight.

The nonionic lipid in formula (I) can, advantageously, also be combined with dicetylphosphate or tetradecylphosphate, especially in the form of a sodium salt, as an addition to the cholesterol.

It is appropriate to state that the total vesicular lipids are made up of the nonionic lipid(s) in formula (I), cholesterol, and, optionally, dicetylphosphate or tetradecylphosphate.

The vesicles are, preferably, obtained from a lipid mixture containing, by weight, 40 to 75 percent of lipids of formula (I), 20 to 50 percent of cholesterol, and 0 to 10 percent (and preferably 50 to 10 percent) of dicetylphosphate or tetradecylphosphate.

The vesicles preferably have average diameters ranging between 25 and 5,000 nm, and in particular between 100 and 500 nm, and they possess, advantageously, a coefficient of polydispersivity of less than 0.4.

The nonionic vesicles are, as is conventionally known, bounded by one or several bi- or multimolecular layers of a nonionic lipid, which layers encapsulate an aqueous phase E. They are dispersed in an aqueous dispersion phase D. According to the present invention, the aqueous phases E and D may be different, but are, preferably, identical.

In accordance with the present invention, the aqueous phase E and/or the aqueous phase D can contain at least one cosmetic additive, such as, principally, a moisturizer, a softening agent, a gelling agent, a preservative, and a filtering agent, and/or at least one pharmaceutically active ingredient, such as an antibiotic or an anti-inflammatory agent.

The lipidic layers can contain at least one liposoluble cosmetic additive and/or at least one liposoluble pharmaceutically active additive.

The nonionic vesicles of the compositions according to the present invention are prepared using any conventional procedure which produces a dispersion of vesicles in an aqueous phase, a dispersion which can then be subjected to an ultrasound treatment in order to reduce the size of the vesicles. One of the procedures for vesicle production, proposed by Bangham (journal of Molecular Biology, 13, 238 (1965), entails the formation of a thin film of a lipid substance on a surface by means of evaporation of the solvent of a lipid solution, the placement of said surface coated with said film in contact with the aqueous phase, and stirring it to produce a dispersion. As described in FR-A-2 221 122 or Australia 5 310 773, it has also been proposed to add a lipid to an aqueous phase, to lightly heat the mixture, and then to vigorously shake the mixture. FR-A-2 315 991, or U.S. Pat. Nos. 4,897,308 or 4,217,344 proposes placing a lipid capable of swelling in water in contact with an aqueous phase, so as to create a lamellar phase; a dispersion phase is then added, and the mixture is vigorously shaken. Other procedures are, moreover, described, particularly in FR-A-2 543 018, or U.S. Pat. No. 4,608,211 and these procedures can also be used. To modify the aqueous phase E, suitable additives can be added during the swelling phase.

The compositions according to the present invention are administered topically on the portion of the skin on which the wound appears; for example, at the rate of 2 to 8 mg/day/cm².

The tests described below, provided purely as non-limiting illustrations, make the invention more clear.

The various tests were conducted on batches of 40 female wistar rats weighing 230 g each, on the backs of which a dermal incision 1 cm long was made on day D. Five topical applications of the healing product tested were then made during each of days D+5 to D+9. The applications consisted of 0.2 ml/day/rat for a surface area of 50 cm².

The rupture strengths of the scars were then measured at day D+12 using the Instron dynamometer. The activity of the product treated was calculated based on the rupture strength and expressed in percentage increase of the rupture strength when compared with a control test not involving the application of the composition. Thus, by definition, the activity of the control is 0%.

EXAMPLE 1

The tests were conducted using compositions containing 8% total vesicular lipids in water. The vesicles were prepared using the procedure described in French Patent 2 315 992 or U.S. Pat. Nos. 4,897,308 or 4,217,344, based on lipidic mixtures containing 47.5% of nonionic lipids by weight, either A, B, or C, 47.5% of cholesterol, and 5% of sodium dicetylphosphate.

The nonionic lipid:

A has as its formula: $R-O-(CH_2-CHOH-CH_2O)_2H$, wherein R is $C_{16}H_{33}$;

B has as its formula

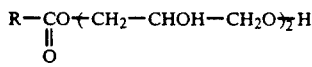

wherein R is $C_{15}H_{31}$; and c has as its formula

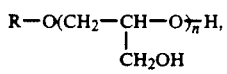

wherein R is $C_{16}H_{33}$ and $\bar{n}$ (average statistical value)=3.

It should be noted that compositions containing vesicles formed with the nonionic lipids A and B are encompassed in the present invention and that those containing vesicles formed using the nonionic lipid C are not part of the invention.

The results given in Table I were obtained. The vesicles prepared using the lipid c give a non-meaningful result, because of measurement inaccuracies. On the other hand, the use of lipids A and B gives a very significant improvement of healing when compared with the untreated control. This healing activity is greater than that provided by a solution containing 5% by weight of acexamic acid or a solution containing 0.1% by weight of human collagen.

TABLE I

| Lipid tested | Average diameter of vesicles | Coefficient* of polydispersivity in diameter | Rupture Strength in cN | Activity |
|---|---|---|---|---|
| A | 136 nm | 0.28 | 461.5 + 18.3 | +52% |
| B | 132 nm | 0.22 | 495.0 + 24.0 | +63% |
| C | 150 nm | 0.23 | 360.2 + 25.7 | +19% |
| Control (no application) | — | — | 303.7 + 17.9 | 0% |

*The coefficient of polydispersivity is a measurement characterizing the homogeneity of the average diameter of the vesicles. It is 0 if all of the vesicles have the same diameter. Beyond 0.4, the polydispersivity is such that the value of the average diameter of the vesicles, calculated using the cumulants method, no longer has any significance.

EXAMPLE 2

Comparative tests were conducted using compositions containing 8% total vesicular lipids by weight in water, while the vesicles contained, by weight, 47.5% of a nonionic lipid A or chimylic alcohol, 47.5% of cholesterol, and 5% of sodium dicetylphosphate. The chimylic alcohol is a glycerol ether having the formula:
R—O—$CH_2CHOHCH_2O$—H, wherein R=$C_{16}H_{33}$, and constitutes a conventional healing and anti-inflammatory agent capable of forming vesicles.

The results are given in Table II, below.

TABLE II

| Lipid | Average diameter of the vesicles | Coefficient of polydispersivity in diameter | Activity |
|---|---|---|---|
| A | 134 nm | 0.23 | +30% |
| Chimylic alcohol | 180 nm | 0.18 | +14% |
| Control (no application) | — | — | 0% |

The result obtained using chimylic alcohol gives nonsignificant values. On the other hand, using lipid A, a significant improvement in healing is observed.

EXAMPLE 3

Effect of vesicle size and influence of the vesicle preparation procedure on healing activity Three tests were conducted using compositions containing 8% total vesicular lipids by weight in water. The vesicles were prepared using lipidic mixtures containing 47.5% of nonionic lipid A, 47.5% of cholesterol, and 5% of sodium dicetylphosphate, by weight.

Tests 1 and 3 were conducted using nonionic vesicles prepared according to a conventional procedure, for example that described in FR-A-2 315 991 or U.S. Pat. Nos. 4,897,308 or 4,217,344, entailing the heat fusion of the lipids, followed by shaking to effect the dispersion in water. Dispersion (1) is tested as is, while dispersion (3) is refined by means of ultrasound. Test 2 was conducted using nonionic vesicles prepared using the procedure entailing formation of a film through solvent evaporation.

The results are recorded in Table III.

TABLE III

| Test | Average diameter of the vesicles | Coefficient of polydispersivity in diameter | Activity |
|---|---|---|---|
| 1 | >1,000 nm | heterogeneous in size | +26% |
| 2 | 189 nm | 0.33 | +43% |
| 3 | 183 nm | 0.31 | +34% |
| Control (no application) | — | — | 0% |

It will be noted that the activity of the nonionic vesicles increases when the size of the vesicles diminishes. On the other hand, the fabrication procedure has no significant influence.

EXAMPLE 4

8% of a mixture containing 47.5% by weight of a nonionic lipid A, 47.5% by weight of cholesterol, and 5% by weight of sodium dicetylphosphate was placed in solution in dipropyleneglycol. Under these conditions, the lipids do not form vesicles.

The healing test shows that the nonionic lipids of the invention, either alone or in combination with cholesterol and dicetylphosphate, placed in solution in a solvent, produce no healing activity.

EXAMPLE 5

3.8% by weight of the nonionic lipids A or B were placed in solution in various solvents. Under these conditions, they do not form vesicles. Healing tests gave the results obtained in Table IV.

A 0% activity rate is obtained, as is, moreover, the case for animals treated with the solvent alone.

TABLE IV

| Lipid | Solvent | Activity |
|---|---|---|
| A | Methylether of dipropylene glycol (*) | 0% |
| B | Methylether of dipropylene glycol (*) | 0% |
| A | Dipropylene glycol | 0% |
| None | Methylether of dipropylene glycol | 0% |
| None | Dipropylene glycol | 0% |
| Control (no application) | — | 0% |

(*) Sold by the Dow Chemical Company under the trade name "DOWANOL DPM".

These tests show that, when the nonionic lipids A and B do not exist as vesicles, they produce no healing action.

EXAMPLE 6

Preparation of a healing lotion

In a stainless-steel beaker, the following products are weighed:

| | |
|---|---|
| Nonionic amphiphilic lipid having the formula given in Example 1: | 3.8 g |
| Cholesterol | 3.8 g |
| Sodium dicetyl phosphate | 0.4 g |

The mixture of these three products is achieved through fusion at a temperature of 110° C. in a nitrogen atmosphere; the temperature of the fused mixture is then reduced to 90° C.

20 g of demineralized water are added. The mixture thus obtained is homogenized at a temperature of 90° C. At this point, 0.3 g of methyl parahydroxybenzoate dissolved in 51.3 g of demineralized water are added.

The mixture is homogenized at a temperature of 70° C. using a "Virtis" ultradisperser until the average size of the vesicles obtained is 200 nm.

Finally, the following substances are added:

| | |
|---|---|
| Mixture of carboxyvinyl acids marketed under the trade name "Carbopol 940" by the Goodrich Company | 0.2 g |
| Triethanolamine | 0.2 g |
| Demineralized water | 20.0 g |

The above lotion is applied on a wound at the rate of 3 mg/day/cm². It is found that, at the end of 12 days, the acute scar-formation phase is completed.

EXAMPLE 7

Healing gel

In a stainless-steel beaker, the following products are weighed:

| | |
|---|---|
| Nonionic amphiphilic lipid having formula A as given in Example 1 | 5.0 g |
| Cholesterol | 5.0 g |

The mixture of these two products is achieved through fusion at 110° in a nitrogen atmosphere; the temperature of the fused mixture is then lowered to 90° C. 20 g of demineralized water are then added.

The mixture obtained is homogenized at 90° C. 0.3 g of methyl parahydroxybenzoate dissolved in 48.88 g of demineralized water is then added.

The mixture is homogenized at 70° C. using a "Virtis" ultradisperser until the average size of the vesicles obtained is 500 nm.

Finally, the following substances are added:

| | |
|---|---|
| Mixture of carboxyvinyl acids marketed under the trade name "Carbopol 940" by the Goodrich Company | 0.42 g |
| Triethanolamine | 0.4 g |
| Demineralized water | 20.0 g |

The above gel is applied on a wound at the rate of 2 mg/day/cm². It is found that, at the end of 12 days, the acute scar-formation phase is completed.

EXAMPLE 8

Healing lotion

In a stainless-steel beaker, the following products are weighed:

| | |
|---|---|
| Nonionic amphiphilic lipid having formula A given in Example 1: | 3.25 g |
| Cholesterol | 1.25 g |
| Sodium dicetyl phosphate | 0.50 g |

The mixture of these three products is achieved through fusion at a temperature of 110° C. in a nitrogen atmosphere; the temperature of the fused mixture is then reduced to 90° C. 10.0 g of demineralized water are added.

The mixture thus obtained is homogenized at a temperature of 90° C. At this point, 0.3 g of methyl parahydroxybenzoate dissolved in 84.7 g of demineralized water are added.

The mixture is homogenized at a temperature of 70° C. using a "Virtis" ultradisperser until the average size of the vesicles obtained is 100 nm.

The dispersion obtained is fluid and can be applied using a pump.

The above lotion is applied on a wound at the rate of 4 mg/day/cm². It is observed that, at the end of 12 days, the acute scar-formation acute phase is completed.

EXAMPLE 9

Healing lotion

In a round 1-liter glass flask, the following products are dissolved in 200 ml of a mixture of chloroform/methanol solvents in the ratio of 2/1:

| | |
|---|---|
| Nonionic amphiphilic lipid having formula B given in Example 1: | 3.8 g |
| Cholesterol | 3.8 g |
| Sodium dicetyl phosphate | 0.4 g |

The solvents are then evaporated using a rotary evaporator, and the final traces of solvent are removed by placing the mixture under the reduced pressure generated by a vane pump for one hour. The combination of lipids is placed in contact with 20 g of demineralized water mixed with 3 g of glycerol.

The mixture is homogenized at 90° C. The following products are then added:

| | |
|---|---|
| Methyl parahydroxybenzoate | 0.3 g |
| Demineralized water | 48.3 g |

This mixture is subjected to the action of a "Virtis" ultradisperser until the size of the vesicles obtained is less than 0.2 micron.

Finally, the following substances are added:

| | |
|---|---|
| Mixture of carboxyvinyl acids marketed under the trade name "Carbopol 940" by the Goodrich Company | 0.2 g |
| Triethanolamine | 0.2 g |

| | |
|---|---|
| -continued | |
| Demineralized water | 20.0 g |

The above lotion is applied on a wound at the rate of 3 mg/day/cm². It is observed that, at the end of 12 days, the acute scar-formation phase is completed.

EXAMPLE 10

Healing gel

In a stainless-steel beaker, the following products are weighed:

| | |
|---|---|
| Nonionic amphiphilic lipid having formula A | 11.875 g |
| Cholesterol | 11.875 g |
| Sodium dicetyl phosphate | 1,250 g |

The mixture of these three products is achieved through fusion at a temperature of 110° C. in a nitrogen atmosphere; the temperature of the fused mixture is then reduced to 90° C. 50.0 9 of demineralized water are added.

The mixture thus obtained is homogenized at a temperature of 90° C. At this point, 0.3 g of methyl parahydroxybenzoate dissolved in 24.7 g of demineralized water are added.

The mixture is homogenized at a temperature of 70° C. using a "Virtis" ultradisperser until the average size of the vesicles obtained is 1,000 nm.

The above gel is applied on a wound at the rate of 2 mg/day/cm². It is observed that, at the end of 12 days, the acute scar-formation phase is completed.

What is claimed is:

1. A process for promoting and accelerating the healing of a wound of living animal tissue reaching the dermis comprising topically applying on the portion of the skin on which the wound appears a healing amount of a composition comprising a dispersion, in an aqueous phase, of vesicles having accelerating wound healing properties, the amphiphilic lipid material of said vesicles consisting of an amphiphilic nonionic lipid consisting of a lipid having the formula $$RO\text{+}CH_2CHOH\text{—}CH_2O\overline{\tau}H \qquad (I)$$

wherein
R represents (1) a $C_{16}$–$C_{18}$ alkyl radical or a mixture thereof or (2) an R'CO radical, wherein R' is at least one $C_{15}$–$C_{17}$ alkyl radical or a mixture thereof, said amphiphilic nonionic lipid being combined with cholesterol, the total vesicular lipid concentration in said composition ranging from 5 to 25 percent by weight based on the total weight of said composition.

2. The process of claim 1 wherein said composition is applied at a rate of 2 to 8 mg of said composition/day/cm².

* * * * *